US006892090B2

(12) United States Patent
Verard et al.

(10) Patent No.: US 6,892,090 B2
(45) Date of Patent: May 10, 2005

(54) METHOD AND APPARATUS FOR VIRTUAL ENDOSCOPY

(75) Inventors: Laurent Verard, Superior, CO (US); Paul Kessman, Broomfield, CO (US); Mark Hunter, Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 218 days.

(21) Appl. No.: 10/223,847

(22) Filed: Aug. 19, 2002

(65) Prior Publication Data

US 2004/0034300 A1 Feb. 19, 2004

(51) Int. Cl.[7] ................................. A61B 5/05
(52) U.S. Cl. ........................ 600/424; 600/427
(58) Field of Search ................. 600/413, 424, 600/425, 426, 427, 429, 431, 407; 128/898, 899, 897; 606/96, 97; 324/307, 308, 309

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,674,014 A | 7/1972 | Tillander |
| 3,702,935 A | 11/1972 | Carey et al. |
| 3,704,707 A | 12/1972 | Halloran |

(Continued)

FOREIGN PATENT DOCUMENTS

| | | |
|---|---|---|
| CA | 964149 | 3/1975 |
| DE | 3042343 A1 | 6/1982 |
| DE | 3831278 A1 | 3/1989 |
| DE | 4233978 C1 | 4/1994 |

(Continued)

OTHER PUBLICATIONS

"Prestige Cervical Disc System Surgical Technique", 12 pgs.
Adams et al., "Orientation Aid for Head and Neck Surgeons," Innov. Tech. Biol. Med., vol. 13, No. 4, 1992, pp. 409–424.

(Continued)

*Primary Examiner*—Daniel I. Robinson
(74) *Attorney, Agent, or Firm*—Harness, Dickey & Pierce, P.L.C.

(57) ABSTRACT

A surgical instrument navigation system is provided that visually simulates a virtual volumetric scene of a body cavity of a patient from a point of view of a surgical instrument residing in the cavity of the patient. The surgical instrument navigation system includes: a surgical instrument; an imaging device which is operable to capture scan data representative of an internal region of interest within a given patient; a tracking subsystem that employs electromagnetic sensing to capture in real-time position data indicative of the position of the surgical instrument; a data processor which is operable to render a volumetric, perspective image of the internal region of interest from a point of view of the surgical instrument; and a display which is operable to display the volumetric perspective image of the patient.

26 Claims, 3 Drawing Sheets

U.S. PATENT DOCUMENTS

| | | |
|---|---|---|
| 3,868,565 A | 2/1975 | Kuipers |
| 3,941,127 A | 3/1976 | Froning |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,202,349 A | 5/1980 | Jones |
| 4,262,306 A | 4/1981 | Renner |
| 4,287,809 A | 9/1981 | Egli et al. |
| 4,314,251 A | 2/1982 | Raab |
| 4,317,078 A | 2/1982 | Weed et al. |
| 4,328,813 A | 5/1982 | Ray |
| 4,339,953 A | 7/1982 | Iwasaki |
| 4,358,856 A | 11/1982 | Stivender et al. |
| 4,368,536 A | 1/1983 | Pfeiler |
| 4,396,885 A | 8/1983 | Constant |
| 4,418,422 A | 11/1983 | Richter et al. |
| 4,422,041 A | 12/1983 | Lienau |
| 4,431,005 A | 2/1984 | McCormick |
| 4,485,815 A | 12/1984 | Amplatz |
| 4,543,959 A | 10/1985 | Sepponen |
| 4,548,208 A | 10/1985 | Niemi |
| 4,572,198 A | 2/1986 | Codrington |
| 4,584,577 A | 4/1986 | Temple |
| 4,613,866 A | 9/1986 | Blood |
| 4,618,978 A | 10/1986 | Cosman |
| 4,621,628 A | 11/1986 | Brudermann |
| 4,625,718 A | 12/1986 | Olerud et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,673,352 A | 6/1987 | Hansen |
| 4,706,665 A | 11/1987 | Gouda |
| 4,719,419 A | 1/1988 | Dawley |
| 4,722,056 A | 1/1988 | Roberts et al. |
| 4,722,336 A | 2/1988 | Kim et al. |
| 4,727,565 A | 2/1988 | Ericson |
| 4,737,794 A | 4/1988 | Jones |
| 4,737,921 A | 4/1988 | Goldwasser et al. |
| 4,750,487 A | 6/1988 | Zanetti |
| 4,771,787 A | 9/1988 | Wurster et al. |
| 4,791,934 A | 12/1988 | Brunnett |
| 4,793,355 A | 12/1988 | Crum et al. |
| 4,797,907 A | 1/1989 | Anderton |
| 4,803,976 A | 2/1989 | Frigg et al. |
| 4,821,206 A | 4/1989 | Arora |
| 4,821,731 A | 4/1989 | Martinelli et al. |
| 4,836,778 A | 6/1989 | Baumrind et al. |
| 4,845,771 A | 7/1989 | Wislocki et al. |
| 4,849,692 A | 7/1989 | Blood |
| 4,862,893 A | 9/1989 | Martinelli |
| 4,889,526 A | 12/1989 | Rauscher et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,099,845 A | 3/1992 | Besz et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,228,442 A | 7/1993 | Imran |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,291,199 A | 3/1994 | Overman et al. |
| 5,295,483 A | 3/1994 | Nowacki et al. |
| 5,297,549 A | 3/1994 | Beatty et al. |
| 5,299,254 A | 3/1994 | Dancer et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,333,168 A | 7/1994 | Fernandes et al. |

| | | | | | | |
|---|---|---|---|---|---|---|
| 5,353,795 A | 10/1994 | Souza et al. | | 5,583,909 A | 12/1996 | Hanover |
| 5,353,800 A | 10/1994 | Pohndorf et al. | | 5,588,430 A | 12/1996 | Bova et al. |
| 5,353,807 A | 10/1994 | DeMarco | | 5,592,939 A | 1/1997 | Martinelli |
| 5,368,030 A | 11/1994 | Zinreich et al. | | 5,595,193 A | 1/1997 | Walus et al. |
| 5,375,596 A | 12/1994 | Twiss et al. | | 5,596,228 A | 1/1997 | Anderton et al. |
| 5,377,678 A | 1/1995 | Dumoulin et al. | | 5,600,330 A | 2/1997 | Blood |
| 5,383,454 A | 1/1995 | Bucholz | | 5,603,318 A | 2/1997 | Heilbrun et al. |
| 5,385,146 A | 1/1995 | Goldreyer | | 5,617,462 A | 4/1997 | Spratt |
| 5,385,148 A | 1/1995 | Lesh et al. | | 5,617,857 A | 4/1997 | Chader et al. |
| 5,386,828 A | 2/1995 | Owens et al. | | 5,619,261 A | 4/1997 | Anderton |
| 5,389,101 A | 2/1995 | Heilbrun et al. | | 5,622,169 A | 4/1997 | Golden et al. |
| 5,391,199 A | 2/1995 | Ben-Haim | | 5,622,170 A | 4/1997 | Schulz |
| 5,394,457 A | 2/1995 | Leibinger et al. | | 5,627,873 A | 5/1997 | Hanover et al. |
| 5,397,329 A | 3/1995 | Allen | | 5,628,315 A | 5/1997 | Vilsmeier et al. |
| 5,399,146 A | 3/1995 | Nowacki et al. | | 5,630,431 A | 5/1997 | Taylor |
| 5,400,384 A | 3/1995 | Fernandes et al. | | 5,636,644 A | 6/1997 | Hart et al. |
| 5,402,801 A | 4/1995 | Taylor | | 5,638,819 A | 6/1997 | Manwaring et al. |
| 5,403,321 A | 4/1995 | DiMarco | | 5,640,170 A | 6/1997 | Anderson |
| 5,408,409 A | 4/1995 | Glassman et al. | | 5,642,395 A | 6/1997 | Anderton et al. |
| 5,417,210 A | 5/1995 | Funda et al. | | 5,643,268 A | 7/1997 | Vilsmeier et al. |
| 5,419,325 A | 5/1995 | Dumoulin et al. | | 5,645,065 A | 7/1997 | Shapiro et al. |
| 5,423,334 A | 6/1995 | Jordan | | 5,647,361 A | 7/1997 | Damadian |
| 5,425,367 A | 6/1995 | Shapiro et al. | | 5,662,111 A | 9/1997 | Cosman |
| 5,425,382 A | 6/1995 | Golden et al. | | 5,664,001 A | 9/1997 | Tachibana et al. |
| 5,426,683 A | 6/1995 | O'Farrell, Jr. et al. | | 5,674,296 A | 10/1997 | Bryan et al. |
| 5,426,687 A | 6/1995 | Goodall et al. | | 5,676,673 A | 10/1997 | Ferre et al. |
| 5,427,097 A | 6/1995 | Depp | | 5,681,260 A | 10/1997 | Ueda et al. |
| 5,429,132 A | 7/1995 | Guy et al. | | 5,682,886 A | 11/1997 | Delp et al. |
| 5,433,198 A | 7/1995 | Desai | | 5,690,108 A | 11/1997 | Chakeres |
| RE35,025 E | 8/1995 | Anderton | | 5,694,945 A | 12/1997 | Ben-Haim |
| 5,437,277 A | 8/1995 | Dumoulin et al. | | 5,695,500 A | 12/1997 | Taylor et al. |
| 5,443,066 A | 8/1995 | Dumoulin et al. | | 5,695,501 A | 12/1997 | Carol et al. |
| 5,443,489 A | 8/1995 | Ben-Haim | | 5,697,377 A | 12/1997 | Wittkampf |
| 5,444,756 A | 8/1995 | Pai et al. | | 5,702,406 A | 12/1997 | Vilsmeier et al. |
| 5,445,144 A | 8/1995 | Wodicka et al. | | 5,704,897 A * | 1/1998 | Truppe ...................... 600/117 |
| 5,445,150 A | 8/1995 | Dumoulin et al. | | 5,711,299 A | 1/1998 | Manwaring et al. |
| 5,445,166 A | 8/1995 | Taylor | | 5,713,946 A | 2/1998 | Ben-Haim |
| 5,446,548 A | 8/1995 | Gerig et al. | | 5,715,822 A | 2/1998 | Watkins |
| 5,447,154 A | 9/1995 | Cinquin et al. | | 5,715,836 A | 2/1998 | Kliegis et al. |
| 5,448,610 A | 9/1995 | Yamamoto et al. | | 5,718,241 A | 2/1998 | Ben-Haim et al. |
| 5,453,686 A | 9/1995 | Anderson | | 5,727,552 A | 3/1998 | Ryan |
| 5,456,718 A | 10/1995 | Szymaitis | | 5,727,553 A | 3/1998 | Saad |
| 5,458,718 A | 10/1995 | Venkitachalam | | 5,729,129 A | 3/1998 | Acker |
| 5,464,446 A | 11/1995 | Dreessen et al. | | 5,730,129 A | 3/1998 | Darrow et al. |
| 5,478,341 A | 12/1995 | Cook et al. | | 5,730,130 A | 3/1998 | Fitzpatrick et al. |
| 5,478,343 A | 12/1995 | Ritter | | 5,732,703 A | 3/1998 | Kalfas et al. |
| 5,480,422 A | 1/1996 | Ben-Haim | | 5,735,278 A | 4/1998 | Hoult et al. |
| 5,483,961 A | 1/1996 | Kelly et al. | | 5,738,096 A | 4/1998 | Ben-Haim |
| 5,485,849 A | 1/1996 | Panescu et al. | | 5,740,267 A | 4/1998 | Echerer et al. |
| 5,487,391 A | 1/1996 | Panescu | | 5,741,214 A | 4/1998 | Ouchi et al. |
| 5,487,729 A | 1/1996 | Avellanet et al. | | 5,742,394 A | 4/1998 | Hansen |
| 5,487,757 A | 1/1996 | Truckai et al. | | 5,744,953 A | 4/1998 | Hansen |
| 5,490,196 A | 2/1996 | Rudich et al. | | 5,748,767 A | 5/1998 | Raab |
| 5,494,034 A | 2/1996 | Schlondorff et al. | | 5,749,362 A | 5/1998 | Funda et al. |
| 5,503,416 A | 4/1996 | Aoki et al. | | 5,749,835 A | 5/1998 | Glantz |
| 5,513,637 A | 5/1996 | Twiss et al. | | 5,752,513 A | 5/1998 | Acker et al. |
| 5,515,160 A | 5/1996 | Schulz et al. | | 5,755,725 A | 5/1998 | Druais |
| 5,517,990 A | 5/1996 | Kalfas et al. | | RE35,816 E | 6/1998 | Schulz |
| 5,531,227 A | 7/1996 | Schneider | | 5,758,667 A | 6/1998 | Slettenmark |
| 5,531,520 A | 7/1996 | Grimson et al. | | 5,762,064 A | 6/1998 | Polyani |
| 5,542,938 A | 8/1996 | Avellanet et al. | | 5,767,669 A | 6/1998 | Hansen et al. |
| 5,543,951 A | 8/1996 | Moehrmann | | 5,769,789 A | 6/1998 | Wang et al. |
| 5,546,940 A | 8/1996 | Panescu et al. | | 5,769,861 A | 6/1998 | Vilsmeier |
| 5,546,949 A | 8/1996 | Frazin et al. | | 5,772,594 A | 6/1998 | Barrick |
| 5,546,951 A | 8/1996 | Ben-Haim | | 5,775,322 A | 7/1998 | Silverstein et al. |
| 5,551,429 A | 9/1996 | Fitzpatrick et al. | | 5,776,050 A | 7/1998 | Chen et al. |
| 5,558,091 A | 9/1996 | Acker et al. | | 5,776,064 A | 7/1998 | Kalfas et al. |
| 5,568,809 A | 10/1996 | Ben-haim | | 5,782,765 A | 7/1998 | Jonkman |
| 5,572,999 A | 11/1996 | Funda et al. | | 5,787,886 A | 8/1998 | Kelly et al. |
| 5,573,533 A | 11/1996 | Strul | | 5,792,055 A | 8/1998 | McKinnon |
| 5,575,794 A | 11/1996 | Walus et al. | | 5,795,294 A | 8/1998 | Luber et al. |

| Patent No. | Date | Inventor |
|---|---|---|
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,728 A | 9/1998 | Kuhn |
| 5,810,735 A | 9/1998 | Halperin et al. |
| 5,823,192 A | 10/1998 | Kalend et al. |
| 5,823,958 A | 10/1998 | Truppe |
| 5,828,725 A | 10/1998 | Levinson |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,884,410 A | 3/1999 | Prinz |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,981 A | 9/1999 | Cosman |
| 5,950,629 A | 9/1999 | Taylor et al. |
| 5,951,475 A | 9/1999 | Gueziec et al. |
| 5,954,647 A | 9/1999 | Bova et al. |
| 5,964,796 A | 10/1999 | Imran |
| 5,967,980 A | 10/1999 | Ferre et al. |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,073,043 A | 6/2000 | Schneider |
| 6,104,944 A | 8/2000 | Martinelli |
| 6,112,113 A | 8/2000 | Van Der Brug et al. |
| 6,118,845 A | 9/2000 | Simon et al. |
| 6,122,538 A | 9/2000 | Sliwa, Jr. et al. |
| 6,131,396 A | 10/2000 | Duerr et al. |
| 6,135,946 A | 10/2000 | Konen et al. |
| 6,139,183 A | 10/2000 | Graumann |
| 6,144,874 A * | 11/2000 | Du .................. 600/413 |
| 6,149,592 A | 11/2000 | Yanof et al. |
| 6,156,067 A | 12/2000 | Bryan et al. |
| 6,161,032 A | 12/2000 | Acker |
| 6,167,296 A * | 12/2000 | Shahidi .................. 600/427 |
| 6,172,499 B1 | 1/2001 | Ashe |
| 6,175,756 B1 | 1/2001 | Ferre et al. |
| 6,216,026 B1 | 4/2001 | Kuhn et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,205 B1 | 5/2001 | Ludeke et al. |
| 6,246,231 B1 | 6/2001 | Ashe |
| 6,252,599 B1 | 6/2001 | Natsuko et al. |
| 6,273,896 B1 | 8/2001 | Franck et al. |
| 6,298,262 B1 | 10/2001 | Franck et al. |
| 6,332,089 B1 | 12/2001 | Acker et al. |
| 6,341,231 B1 | 1/2002 | Ferre et al. |
| 6,346,940 B1 | 2/2002 | Fukunaga |
| 6,351,659 B1 | 2/2002 | Vilsmeier |
| 6,369,812 B1 | 4/2002 | Iyriboz et al. |
| 6,374,134 B1 | 4/2002 | Bladen et al. |
| 6,380,958 B1 | 4/2002 | Guendel et al. |
| 6,381,485 B1 * | 4/2002 | Hunter et al. .................. 600/407 |
| 6,424,856 B1 | 7/2002 | Vilsmeier et al. |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,442,417 B1 * | 8/2002 | Shahidi et al. .................. 600/429 |
| 6,445,943 B1 | 9/2002 | Ferre et al. |
| 6,456,735 B1 | 9/2002 | Sato et al. |
| 6,470,207 B1 | 10/2002 | Simon et al. |
| 6,471,653 B1 | 10/2002 | Jordfald et al. |
| 6,474,341 B1 * | 11/2002 | Hunter et al. .................. 128/899 |
| 6,478,743 B1 | 11/2002 | Jordfald et al. |
| 6,484,049 B1 | 11/2002 | Seeley et al. |
| 6,490,475 B1 | 12/2002 | Seeley et al. |
| 6,493,573 B1 * | 12/2002 | Martinelli et al. .................. 600/424 |
| 6,494,843 B2 | 12/2002 | Edwardsen et al. |
| 6,496,188 B1 | 12/2002 | Deschamps et al. |
| 6,498,944 B1 | 12/2002 | Ben-Haim et al. |
| 6,499,488 B1 * | 12/2002 | Hunter et al. .................. 128/899 |
| 6,511,417 B1 | 1/2003 | Taniguchi et al. |
| 6,511,418 B2 | 1/2003 | Shahidi et al. |
| 6,517,478 B2 | 2/2003 | Khadem |
| 6,522,324 B1 | 2/2003 | Bosma et al. |
| 6,522,907 B1 | 2/2003 | Bladen et al. |
| 6,527,443 B1 | 3/2003 | Vilsmeier et al. |
| 6,529,758 B2 | 3/2003 | Shahidi |
| 6,546,278 B2 * | 4/2003 | Walsh .................. 600/428 |
| 6,547,739 B2 | 4/2003 | Jordfald et al. |
| 6,551,325 B2 | 4/2003 | Neubauer et al. |
| 6,556,695 B1 | 4/2003 | Packer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,636,575 B1 * | 10/2003 | Ott .................. 375/376 |
| 6,640,128 B2 | 10/2003 | Vilsmeier et al. |
| 6,694,162 B2 | 2/2004 | Hartlep |
| 6,701,179 B1 * | 3/2004 | Martinelli et al. .................. 600/424 |
| 2001/0007919 A1 | 7/2001 | Shahidi |
| 2001/0016684 A1 | 8/2001 | Shahidi |
| 2001/0025183 A1 | 9/2001 | Shahidi |
| 2001/0029333 A1 | 10/2001 | Shahidi |
| 2001/0031919 A1 | 10/2001 | Stommer et al. |
| 2001/0037064 A1 | 11/2001 | Shahidi |
| 2002/0010384 A1 | 1/2002 | Shahidi et al. |
| 2002/0049375 A1 | 4/2002 | Strommer et al. |
| 2002/0055674 A1 | 5/2002 | Fenster et al. |

| | | | |
|---|---|---|---|
| 2002/0075994 | A1 | 6/2002 | Shahidi et al. |
| 2002/0077543 | A1 | 6/2002 | Grzeszczuk et al. |
| 2002/0077544 | A1 | 6/2002 | Shahidi |
| 2003/0032878 | A1 | 2/2003 | Shahidi |
| 2003/0083567 | A1 | 5/2003 | Deschamps |

FOREIGN PATENT DOCUMENTS

| | | |
|---|---|---|
| DE | 10085137 | 11/2002 |
| EP | 0 319 844 A1 | 1/1988 |
| EP | 0419729 A1 | 9/1989 |
| EP | 0350996 A1 | 1/1990 |
| EP | 0 651 968 A1 | 8/1990 |
| EP | 0 581 704 B1 | 7/1993 |
| EP | 0655138 B1 | 8/1993 |
| EP | 0894473 A2 | 1/1995 |
| FR | 2417970 | 2/1979 |
| JP | 2765738 | 6/1998 |
| WO | WO 88/09151 | 12/1988 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 96/11624 | 4/1996 |
| WO | WO 98/08554 | 3/1998 |
| WO | WO 98/38908 | 9/1998 |
| WO | WO99/00052 | 1/1999 |
| WO | WO 89/05123 | 6/1999 |
| WO | WO99/38449 | 8/1999 |
| WO | WO 99/60939 | 12/1999 |
| WO | WO 01/30437 A1 | 5/2001 |
| WO | WO01/37748 | 5/2001 |

OTHER PUBLICATIONS

Barrick et al., "Prophylactic Intramedullary Fixation of the Tibia for Stress Fracture in a Professional Athlete," Journal of Orthopaedic Trauma, vol. 6, No. 2, pp. 241–244 (1992).

Barrick et al., "Technical Difficulties with the Brooker–Wills Nail in Acute Fractures of the Femur," Journal of Orthopaedic Trauma, vol. 6, No. 2, pp. 144–150 (1990).

Barrick, "Distal Locking Screw Insertion Using a Cannulated Drill Bit: Technical Note," Journal of Orthopaedic Trauma, vol. 7, No. 3, 1993, pp. 248–251.

Batnitzky et al., "Three–Dimensional Computer Reconstructions of Brain Lesions from Surface Contours Provided by Computed Tomography: A Prospectus," Neurosurgery, vol. 11, No. 1, Part 1, 1982, pp. 73–84.

Benzel et al., "Magnetic Source Imaging: a Review of the Magnes System of Biomagnetic Technologies Incorporated," Neurosurgery, vol. 33, No. 2 (Aug. 1993), pp. 252–259.

Bouazza–Marouf et al.; "Robotic–Assisted Internal Fixation of Femoral Fractures", IMECHE., pp. 51–58 (1995).

Brack et al., "Accurate X–ray Based Navigation in Computer–Assisted Orthopedic Surgery," CAR '98, pp. 716–722.

Bryan, "Bryan Cervical Disc System Single Level Surgical Technique", Spinal Dynamics, 2022, pp. 1–33.

Bucholz et al., "Variables affecting the accuracy of stereotactic localizationusing computerized tomography," Journal of Neurosurgery, vol. 79, Nov. 1993, pp. 667–673.

Champleboux et al., "Accurate Calibration of Cameras and Range Imaging Sensors: the NPBS Method," IEEE International Conference on Robotics and Automation, Nice, France, May, 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254–263.

Cinquin et al., "Computer Assisted Medical Interventions," International Advanced Robotics Programme, Sep. 1989, pp. 63–65.

Clarysse et al., "A Computer–Assisted System for 3–D Frameless Localization in Stereotaxic MRI," IEEE Transactions on Medical Imaging, vol. 10, No. 4, Dec. 1991, pp. 523–529.

Feldmar et al., "3D–2D Projective Registration of Free–Form Curves and Surfaces," Rapport de recherche (Inria Sophia Antipolis), 1994, pp. 1–44.

Foley et al., "Fundamentals of Interactive Computer Graphics," The Systems Programming Series, Chapter 7, Jul. 1984, pp. 245–266.

Foley et al., "Image–guided Intraoperative Localization," Intraoperative Neuroprotection, Chapter 19, 1996, pp. 325–340.

Foley, "The StealthStation: Three–Dimensional Image–Interactive Guidance for the Spine Surgeon," Spine Frontiers, Apr. 1996, pp. 7–9.

Gildenberg et al., "Calculation of Stereotactic Coordinates from the Computed Tomographic Scan," Neurosurgery, vol. 10, No. 5, May 1992, pp. 580–586.

Gonzalez, "Digital Image Fundamentals," Digital Image Processing, Second Edition, 1987, pp. 52–54.

Gottesfeld Brown et al., "Registration of Planar Film Radiographs with Computer Tomography," Proceedings of MMBIA, Jun. '96, pp. 42–51.

Gueziec et al., "Registration of Computed Tomography Data to a Surgical Robot Using Fluoroscopy: A Feasibility Study," Computer Science/Mathematics, Sep. 27, 1996, 6 pages.

Hamadeh et al, "Kinematic Study of Lumbar Spine Using Functional Radiographies and 3D/2D Registration," TIMC UMR 5525—IMAG.

Hamadeh et al., "Automated 3–Dimensional Computed Tomographic and Fluoroscopic Image Registration," Computer Aided Surgery (1998), 3:11–19.

Hamadeh et al., "Towards Automatic Registration Between CT and X–ray Images: Cooperation Between 3D/2D Registration and 2D Edge Detection," MRCAS '95, pp. 39–46.

Hatch, "Reference–Display System for the Integration of CT Scanning and the Operating Microscope," Thesis, Thayer School of Engineering, Oct. 1984, pp. 1–189.

Heilbrun et al., "Preliminary experience with Brown–Roberts–Wells (BRW) computerized tomography stereotaxic guidance system," Journal of Neurosurgery, vol. 59, Aug. 1983, pp. 217–222.

Henderson et al., "An Accurate and Ergonomic Method of Registration for Image–guided Neurosurgery," Computerized Medical Imaging and Graphics, vol. 18, No. 4, Jul.–Aug. 1994, pp. 273–277.

Hoerenz, "The Operating Microscope I. Optical Principles, Illumination Systems, and Support Systems," Journal of Microsurgery, vol. 1, 1980, pp. 364–369.

Hofstetter et al., "Fluoroscopy Based Surgical Navigation—Concept and Clinical Applications," Computer Assisted Radiology and Surgery, 1997, pp. 956–960.

Horner et al., "A Comparison of CT–Stereotaxic Brain Biopsy Techniques," Investigative Radiology, Sep.–Oct. 1984, pp. 367–373.

Hounsfield, "Computerized transverse axial scanning (tomography): Part 1. Description of system," British Journal of Radiology, vol. 46, No. 552, Dec. 1973, pp. 1016–1022.

Jacques et al., "A Computerized Microstereotactic Method to Approach, 3–Dimensionally Reconstruct, Remove and Adjuvantly Treat Small CNS Lesions," Applied Neurophysiology, vol. 43, 1980, pp. 176–182.

Jacques et al., "Computerized three–dimensional stereotaxic removal of small central nervous system lesion in patients," J. Neurosurg., vol. 53, Dec. 1980, pp. 816–820.

Joskowicz et al., "Computer–Aided Image–Guided Bone Fracture Surgery: Concept and Implementation," CAR '98, pp. 710–715.

Kelly et al., "Computer–assisted stereotaxic laser resection of intra–axial brain neoplasms," Journal of Neurosurgery, vol. 64, Mar. 1986, pp. 427–439.

Kelly et al., "Precision Resection of Intra–Axial CNS Lesions by CT–Based Stereotactic Craniotomy and Computer Monitored CO2 Laser," Acta Neurochirurgica, vol. 68, 1983, pp. 1–9.

Laitinen et al., "An Adapter for Computed Tomography–Guided, Stereotaxis," Surg. Neurol., 1985, pp. 559–566.

Laitinen, "Noninvasive multipurpose stereoadapter," Neurological Research, Jun. 1987, pp. 137–141.

Lavallee et al, "Matching 3–D Smooth Surfaces with their 2–D Projections using 3–D Distance Maps," SPIE, vol. 1570, Geometric Methods in Computer Vision, 1991, pp. 322–336.

Lavallee et al., "Computer Assisted Driving of a Needle into the Brain," Proceedings of the International Symposium CAR '89, Computer Assisted Radiology, 1989, pp. 416–420.

Lavallee et al., "Computer Assisted Interventionist Imaging: The Instance of Stereotactic Brain Surgery," North–Holland MEDINFO 89, Part 1, 1989, pp. 613–617.

Lavallee et al., "Computer Assisted Spine Surgery: A Technique For Accurate Transpedicular Screw Fixation Using CT Data and a 3–D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618–624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926–0927.

Lavallee, "VI Adaption de la Methodologie a Quelques Applications Cliniques," Chapitre VI, pp. 133–148.

Leksell et al., "Stereotaxis and Tomography—A Technical Note," ACTA Neurochirurgica, vol. 52, 1980, pp. 1–7.

Lemieux et al., "A Patient–to–Computed–Tomography Image Registration Method Based on Digitally Reconstructed Radiographs," Med. Phys. 21 (11), Nov. 1994, pp. 1749–1760.

Levin et al., "The Brain: Integrated Three–dimensional Display of MR and PET Images," Radiology, vol. 172, No. 3, Sep. 1989, pp. 783–789.

Mazier et al., "Computer–Assisted Interventionist Imaging: Application to the Vertebral Column Surgery," Annual International Conference of the IEEE Engineering in Medicine and Biology Society, vol. 12, No. 1, 1990, pp. 0430–0431.

Mazier et al., Chirurgie de la Colonne Vertebrale Assistee par Ordinateur: Application au Vissage Pediculaire, Innov. Tech. Biol. Med., vol. 11, No. 5, 1990, pp. 559–566.

Pelizzari et al., "Accurate Three–Dimensional Registration of CT, PET, and/or MR Images of the Brain," Journal of Computer Assisted Tomography, Jan./Feb. 1989, pp. 20–26.

Pelizzari et al., "Interactive 3D Patient–Image Registration," Information Processing in Medical Imaging, 12th International Conference, IPMI '91, Jul. 7–12, 136–141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251–264.

Potamianos et al., "Intra–Operative Imaging Guidance for Keyhole Surgery Methodology and Calibration," First International Symposium on Medical Robotics and Computer Assisted Surgery, Sep. 22–24, 1994, pp. 98–104.

Reinhardt et al., "CT–Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545–549.

Rosenbaum et al., "Computerized Tomography Guided Stereotaxis: A New Approach," Applied Neurophysiology, vol. 43, No. 3–5, 1980, pp. 172–173.

Sautot, "Vissage Pediculaire Assiste Par Ordinateur," Sep. 20, 1994.

Schueler et al., "Correction of Image Intensifier Distortion for Three–Dimensional X–Ray Angiography," SPIE Medical Imaging 1995, vol. 2432, pp. 272–279.

Selvik et al., "A Roentgen Stereophotogrammetric System," Acta Radiologica Diagnosis, 1983, pp. 343–352.

Shelden et al., "Development of a computerized microsteroetaxic method for localization and removal of minute CNS lesions under direct 3–D vision," J. Neurosurg., vol. 52, 1980, pp. 21–27.

Smith et al., "Computer Methods for Improved Diagnostic Image Display Applied to Stereotactic Neurosurgery," Automedical, vol. 14, 1992, pp. 371–382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.–Aug. 1994, pp. 247–256.

The Laitinen Stereotactic System, E2–E6.

Viant et al., "A Computer Assisted Orthopaedic System for Distal Locking of Intramedullary Nails," Proc. of MediMEC '95, Bristol, 1995, pp. 86–91.

Watanabe et al., "Three–Dimensional Digitizer (Neuronavigator): New Equipment for Computed Tomography–Guided Stereotaxic Surgery," Surgical Neurology, vol. 27, No. 6, Jun. 1987, pp. 543–547.

Watanabe, "Neuronavigator," Igaku–no–Ayumi, vol. 137, No. 6, May 10, 1986, pp. 1–4.

Weese et al., "An Approach to 2D/3D Registration of a Vertebra in 2D X–ray Fluoroscopies with 3D CT Images," pp. 119–128.

Germano, "Instrumentation, Technique and Technology", Neurosurgery, vol. 37, No. 2, Aug., 1995, pp. 348–350.

Merloz, et al., "Computer Assisted Spine Surgery", Clinical Assisted Spine Surgery, No. 337, pp. 86–96.

Hatch, et al., "Reference–Display System for the Integration of CT Scanning and the Operating Microscope", Proceedings of the Eleventh Annual Northeast Bioengineering Conference, Mar. 14–15, 1985, pp. 252–254.

European Search Report for EP 03 01 8301 dated Oct. 23, 2003.

* cited by examiner

US 6,892,090 B2

METHOD AND APPARATUS FOR VIRTUAL ENDOSCOPY

FIELD OF THE INVENTION

The present invention relates generally to surgical instrument navigation systems and, more particularly, to a system that visually simulates a virtual volumetric scene of a body cavity from a point of view of a surgical instrument residing in a patient.

BACKGROUND OF THE INVENTION

Precise imaging of portions of the anatomy is an increasingly important technique in the medical and surgical fields. In order to lessen the trauma to a patient caused by invasive surgery, techniques have been developed for performing surgical procedures within the body through small incisions with minimal invasion. These procedures generally require the surgeon to operate on portions of the anatomy that are not directly visible, or can be seen only with difficulty. Furthermore, some parts of the body contain extremely complex or small structures and it is necessary to enhance the visibility of these structures to enable the surgeon to perform more delicate procedures. In addition, planning such procedures required the evaluation of the location and orientation of these structures within the body in order to determine the optimal surgical trajectory.

Endoscopy is one commonly employed technique for visualizing internal regions of interest within a patient. Flexible endoscopes enable surgeons to visually inspect a region prior to or during surgery. However, flexible endoscopes are relatively expensive, limited in flexibility due to construction and obscured by blood and other biological materials.

Therefore, it is desirable to provide a cost effective alternative technique for visualizing an internal regions of interest within a patient.

SUMMARY OF THE INVENTION

In accordance with the present invention, a surgical instrument navigation system is provided that visually simulates a virtual volumetric scene of a body cavity of a patient from a point of view of a surgical instrument residing in the patient. The surgical instrument navigation system generally includes: a surgical instrument, such as a guide wire or catheter; a tracking subsystem that captures real-time position data indicative of the position (location and/or orientation) of the surgical instrument; a data processor which is operable to render a volumetric image of the internal region of interest from a point of view of the surgical instrument; and a display which is operable to display the volumetric image of the patient. The surgical instrument navigation system may also include an imaging device which is operable to capture 2D and/or 3D volumetric scan data representative of an internal region of interest within a given patient.

For a more complete understanding of the invention, reference may be made to the following specification and to the accompanying drawings.

DETAILED DESCRIPTION OF THE PREFERRED EMBODIMENTS

Figure 1:
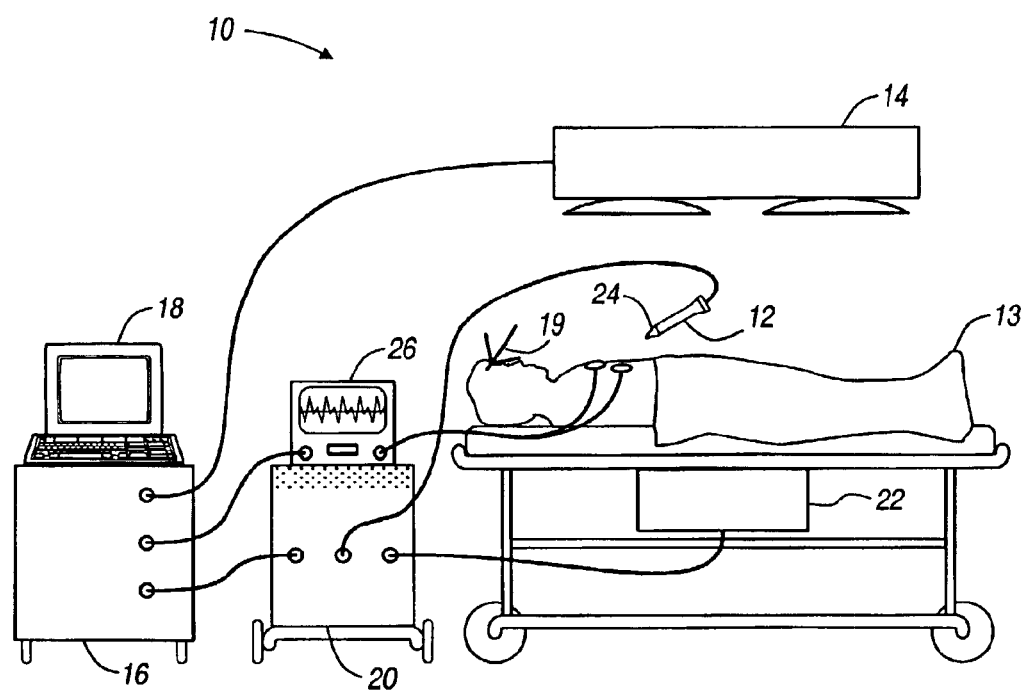
FIG. 1 is a diagram of an exemplary surgical instrument navigation system in accordance with present invention.

FIG. 1 is a diagram of an exemplary surgical instrument navigation system 10. In accordance with one aspect of the present invention, the surgical instrument navigation system 10 is operable to visually simulate a virtual volumetric scene within the body of a patient, such as an internal body cavity, from a point of view of a surgical instrument 12 residing in the cavity of a patient 13. To do so, the surgical instrument navigation system 10 is primarily comprised of a surgical instrument 12, a data processor 16 having a display 18, and a tracking subsystem 20. The surgical instrument navigation system 10 may further include (or accompanied by) an imaging device 14 that is operable to provide image data to the system.

The surgical instrument 12 is preferably a relatively inexpensive, flexible and/or steerable catheter that may be of a disposable type. The surgical instrument 12 is modified to include one or more tracking sensors that are detectable by the tracking subsystem 20. It is readily understood that other types of surgical instruments (e.g., a guide wire, a pointer probe, a stent, a seed, an implant, an endoscope, etc.) are also within the scope of the present invention. It is also envisioned that at least some of these surgical instruments may be wireless or have wireless communications links. It is also envisioned that the surgical instruments may encompass medical devices which are used for exploratory purposes, testing purposes or other types of medical procedures.

Figure 2:
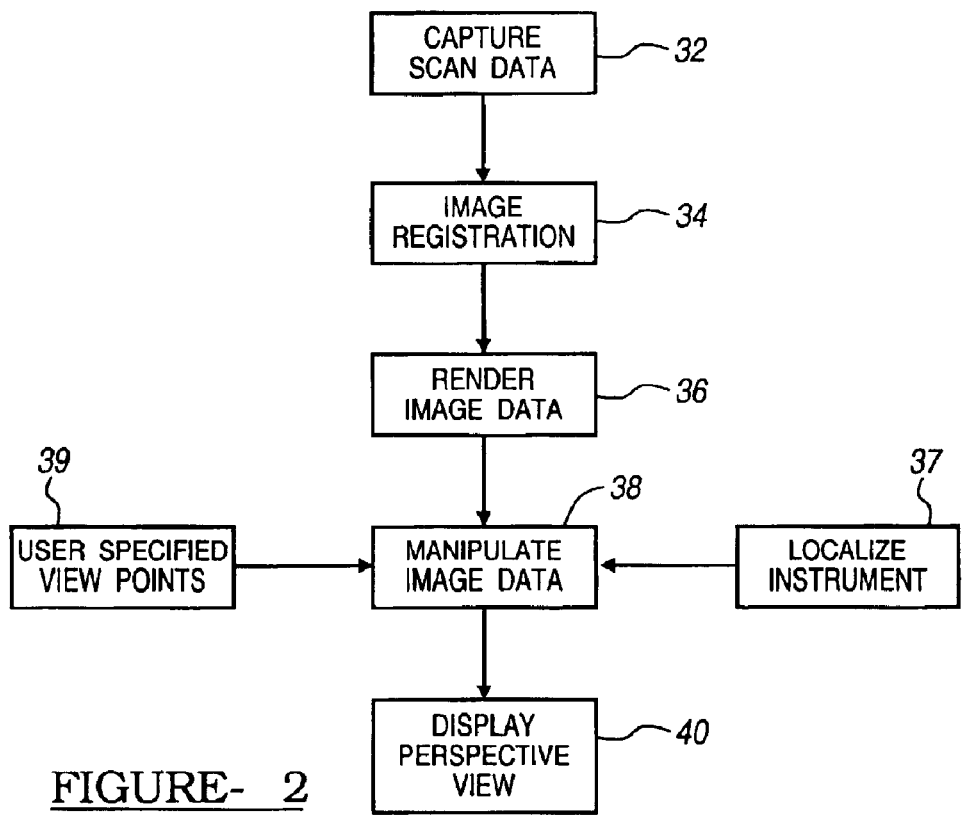
FIG. 2 is a flowchart that depicts a technique for simulating a virtual volumetric scene of a body cavity from a point of view of a surgical instrument positioned within the patient in accordance with the present invention.

Referring to FIG. 2, the imaging device 14 is used to capture volumetric scan data 32 representative of an internal region of interest within the patient 13. The three-dimensional scan data is preferably obtained prior to surgery on the patient 13. In this case, the captured volumetric scan data may be stored in a data store associated with the data processor 16 for subsequent processing. However, one skilled in the art will readily recognize that the principles of the present invention may also extend to scan data acquired during surgery. It is readily understood that volumetric scan data may be acquired using various known medical imaging devices 14, including but not limited to a magnetic resonance imaging (MRI) device, a computed tomography (CT) imaging device, a positron emission tomography (PET) imaging device, a 2D or 3D fluoroscopic imaging device, and 2D, 3D or 4D ultrasound imaging devices. In the case of a two-dimensional ultrasound imaging device or other two-dimensional image acquisition device, a series of two-dimensional data sets may be acquired and then assembled into volumetric data as is well known in the art using a two-dimensional to three-dimensional conversion.

A dynamic reference frame 19 is attached to the patient proximate to the region of interest within the patient 13. To the extent that the region of interest is a vessel or a cavity within the patient, it is readily understood that the dynamic reference frame 19 may be placed within the patient 13. To determine its location, the dynamic reference frame 19 is also modified to include tracking sensors detectable by the tracking subsystem 20. The tracking subsystem 20 is operable to determine position data for the dynamic reference frame 19 as further described below.

The volumetric scan data is then registered as shown at 34. Registration of the dynamic reference frame 19 generally relates information in the volumetric scan data to the region of interest associated with the patient. This process is referred to as registering image space to patient space. Often, the image space must also be registered to another image space. Registration is accomplished through knowledge of the coordinate vectors of at least three non-collinear points in the image space and the patient space.

Registration for image guided surgery can be completed by different known techniques. First, point-to-point registration is accomplished by identifying points in an image space and then touching the same points in patient space. These points are generally anatomical landmarks that are easily identifiable on the patient. Second, surface registration involves the user's generation of a surface in patient space by either selecting multiple points or scanning, and then accepting the best fit to that surface in image space by iteratively calculating with the data processor until a surface match is identified. Third, repeat fixation devices entail the user repeatedly removing and replacing a device (i.e., dynamic reference frame, etc.) in known relation to the patient or image fiducials of the patient. Fourth, automatic registration by first attaching the dynamic reference frame to the patient prior to acquiring image data. It is envisioned that other known registration procedures are also within the scope of the present invention, such as that disclosed in U.S. Ser. No. 09/274,972, filed on Mar. 23, 1999, entitled "NAVIGATIONAL GUIDANCE VIA COMPUTER-ASSISTED FLUOROSCOPIC IMAGING", which is hereby incorporated by reference.

During surgery, the surgical instrument 12 is directed by the surgeon to the region of interest within the patient 13. The tracking subsystem 20 preferably employs electro-magnetic sensing to capture position data 37 indicative of the location and/or orientation of the surgical instrument 12 within the patient. The tracking subsystem 20 may be defined as a localizing device 22 and one or more electro-magnetic sensors 24 may be integrated into the items of interest, such as the surgical instrument 12. In one embodiment, the localizing device 22 is comprised of three or more field generators (transmitters) mounted at known locations on a plane surface and the electro-magnetic sensor (receivers) 24 is further defined as a single coil of wire. The positioning of the field generators (transmitter), and the sensors (receivers) may also be reversed, such that the generators are associated with the surgical instrument 12 and the receivers are positioned elsewhere. Although not limited thereto, the localizing device 22 may be affixed to an underneath side of the operating table that supports the patient.

In operation, the field generators generate magnetic fields which are detected by the sensor. By measuring the magnetic fields generated by each field generator at the sensor, the location and orientation of the sensor may be computed, thereby determining position data for the surgical instrument 12. Although not limited thereto, exemplary electro-magnetic tracking subsystems are further described in U.S. Pat. Nos. 5,913,820; 5,592,939; and 6,374,134 which are incorporated herein by reference. In addition, it is envisioned that other types of position tracking devices are also within the scope of the present invention. For instance, non line-of-sight tracking subsystem 20 may be based on sonic emissions or radio frequency emissions. In another instance, a rigid surgical instrument, such as a rigid endoscope may be tracked using a line-of-sight optical-based tracking subsystem (i.e., LED's, passive markers, reflective markers, etc).

Position data such as location and/or orientation data from the tracking subsystem 20 is in turn relayed to the data processor 16. The data processor 16 is adapted to receive position/orientation data from the tracking subsystem 20 and operable to render a volumetric perspective image and/or a surface rendered image of the region of interest. The volumetric perspective and/or surface image is rendered 36 from the scan data 32 using rendering techniques well known in the art. The image data may be further manipulated 38 based on the position/orientation data for the surgical instrument 12 received from tracking subsystem 20. Specifically, the volumetric perspective or surface rendered image is rendered from a point of view which relates to position of the surgical instrument 12. For instance, at least one electro-magnetic sensor 24 may be positioned at the tip of the surgical instrument 12, such that the image is, rendered from a leading point on the surgical instrument. In this way, the surgical instrument navigation system 10 of the present invention is able, for example, to visually simulate a virtual volumetric scene of an internal cavity from the point of view of the surgical instrument 12 residing in the cavity without the use of an endoscope. It is readily understood that tracking two or more electro-magnetic sensors 24 which are embedded in the surgical instrument 12 enables orientation of the surgical instrument 12 to be determined by the system 10.

As the surgical instrument 12 is moved by the surgeon within the region of interest, its position and orientation are tracked and reported on a real-time basis by the tracking subsystem 20. The volumetric perspective image may then be updated by manipulating 38 the rendered image data 36 based on the position of the surgical instrument 12. The manipulated volumetric perspective image is displayed 40 on a display device 18 associated with the data processor 16. The display 18 is preferably located such that it can be easily viewed by the surgeon during the medical procedure. In one embodiment, the display 18 may be further defined as a heads-up display or any other appropriate display. The image may also be stored by data processor 16 for later playback, should this be desired.

It is envisioned that the primary perspective image 38 of the region of interest may be supplemented by other secondary images. For instance, known image processing techniques may be employed to generate various multi-planar images of the region of interest. Alternatively, images may be generated from different view points as specified by a user 39, including views from outside of the vessel or cavity or views that enable the user to see through the walls of the vessel using different shading or opacity. In another instance, the location data of the surgical instrument may be saved and played back in a movie format. It is envisioned that these various secondary images may be displayed simultaneously with or in place of the primary perspective image.

In addition, the surgical instrument 12 may be used to generate real-time maps corresponding to an internal path traveled by the surgical instrument or an external boundary of an internal cavity. Real-time maps are generated by continuously recording the position of the instrument's localized tip and its full extent. A real-time map is generated by the outermost extent of the instrument's position and minimum extrapolated curvature as is known in the art. The map may be continuously updated as the instrument is moved within the patient, thereby creating a path or a volume representing the internal boundary of the cavity. It is envisioned that the map may be displayed in a wire frame form, as a shaded surface or other three-dimensional computer display modality independent from or superimposed on the volumetric perspective image 38 of the region of interest. It is further envisioned that the map may include data collected from a sensor embedded into the surgical instrument, such as pressure data, temperature data or electro-physiological data. In this case, the map may be color coded to represent the collected data.

Figure 3:
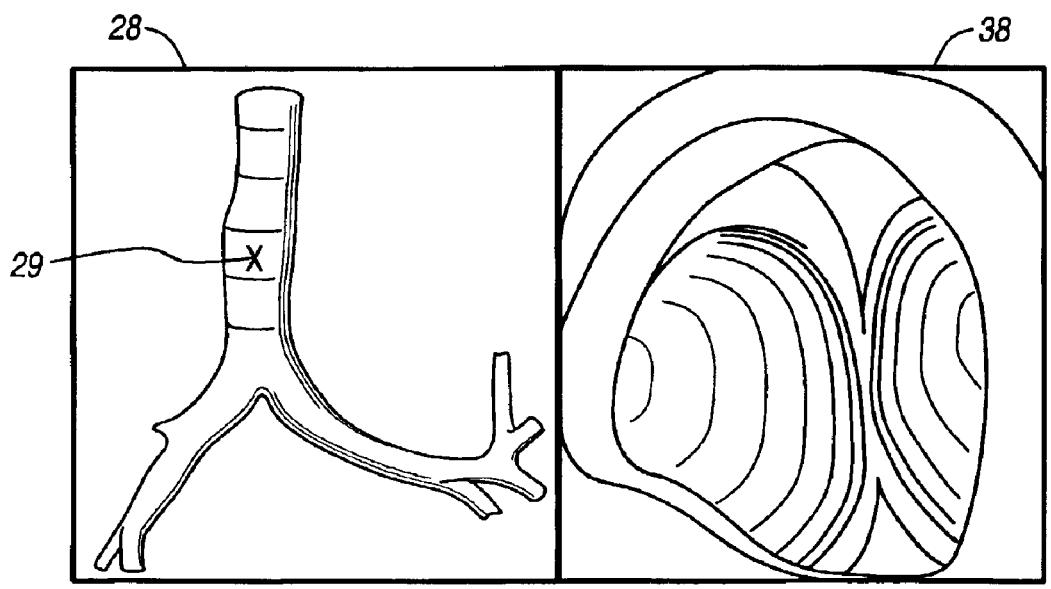
FIG. 3 is an exemplary display from the surgical instrument navigation system of the present invention.

FIG. 3 illustrates another type of secondary image 28 which may be displayed in conjunction with the primary perspective image 38. In this instance, the primary perspective image is an interior view of an air passage within the patient 13. The secondary image 28 is an exterior view of the air passage which includes an indicia or graphical representation 29 that corresponds to the location of the surgical instrument 12 within the air passage. In FIG. 3, the indicia 29 is shown as a crosshairs. It is envisioned that other indicia may be used to signify the location of the surgical instrument in the secondary image. As further described below, the secondary image 28 is constructed by superimposing the indicia 29 of the surgical instrument 12 onto the manipulated image data 38.

Figure 4:
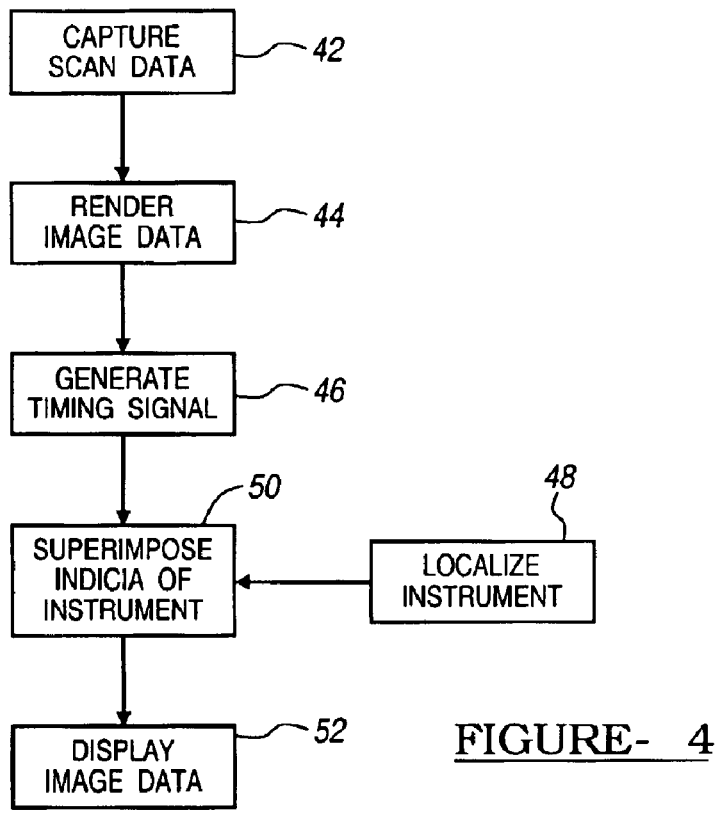
FIG. 4 is a flowchart that depicts a technique for synchronizing the display of an indicia or graphical representation of the surgical instrument with cardiac or respiratory cycle of the patient in accordance with the present invention.

Referring to FIG. 4, the display of an indicia of the surgical instrument 12 on the secondary image may be synchronized with an anatomical function, such as the cardiac or respiratory cycle, of the patient. In certain instances, the cardiac or respiratory cycle of the patient may cause the surgical instrument 12 to flutter or jitter within the patient. For instance, a surgical instrument 12 positioned in or near a chamber of the heart will move in relation to the patient's heart beat. In these instance, the indicia of the surgical instrument 12 will likewise flutter or jitter on the displayed image 40. It is envisioned that other anatomical functions which may effect the position of the surgical instrument 12 within the patient are also within the scope of the present invention.

To eliminate the flutter of the indicia on the displayed image 40, position data for the surgical instrument 12 is acquired at a repetitive point within each cycle of either the cardiac cycle or the respiratory cycle of the patient. As described above, the imaging device 14 is used to capture volumetric scan data 42 representative of an internal region of interest within a given patient. A secondary image may then be rendered 44 from the volumetric scan data by the data processor 16.

In order to synchronize the acquisition of position data for the surgical instrument 12, the surgical instrument navigation system 10 may further include a timing signal generator 26. The timing signal generator 26 is operable to generate and transmit a timing signal 46 that correlates to at least one of (or both) the cardiac cycle or the respiratory cycle of the patient 13. For a patient having a consistent rhythmic cycle, the timing signal might be in the form of a periodic clock signal. Alternatively, the timing signal may be derived from an electrocardiogram signal from the patient 13. One skilled in the art will readily recognize other techniques for deriving a timing signal that correlate to at least one of the cardiac or respiratory cycle or other anatomical cycle of the patient.

As described above, the indicia of the surgical instrument 12 tracks the movement of the surgical instrument 12 as it is moved by the surgeon within the patient 13. Rather than display the indicia of the surgical instrument 12 on a real-time basis, the display of the indicia of the surgical instrument 12 is periodically updated 48 based on the timing signal from the timing signal generator 26. In one exemplary embodiment, the timing generator 26 is electrically connected to the tracking subsystem 20. The tracking subsystem 20 is in turn operable to report position data for the surgical instrument 12 in response to a timing signal received from the timing signal generator 26. The position of the indicia of the surgical instrument 12 is then updated 50 on the display of the image data. It is readily understood that other techniques for synchronizing the display of an indicia of the surgical instrument 12 based on the timing signal are within the scope of the present invention, thereby eliminating any flutter or jitter which may appear on the displayed image 52. It is also envisioned that a path (or projected path) of the surgical instrument 12 may also be illustrated on the displayed image data 52.

Figure 5:
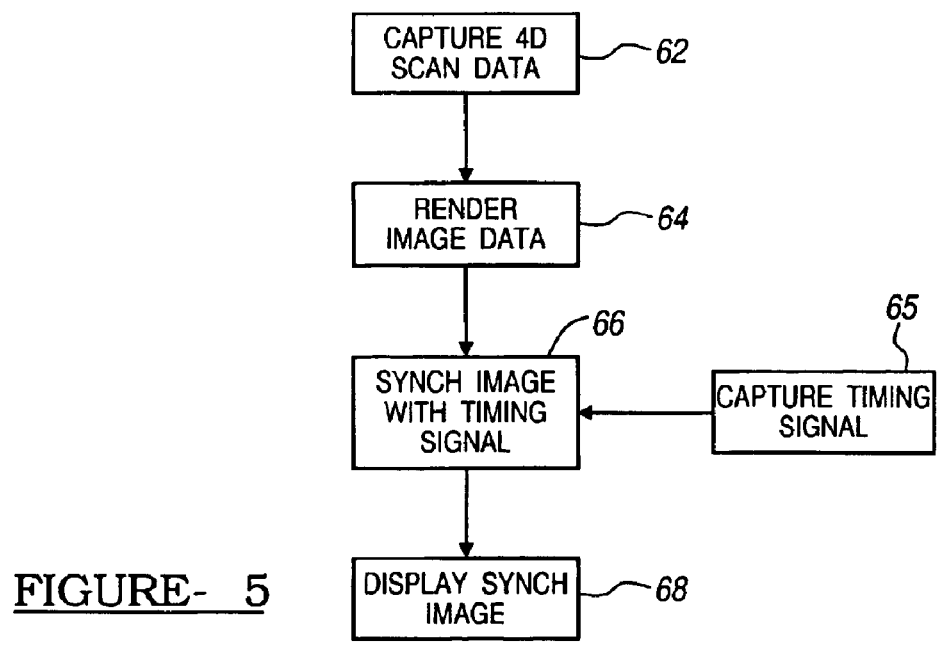
FIG. 5 is a flowchart that depicts a technique for generating four-dimensional image data that is synchronized with the patient in accordance with the present invention.

In another aspect of the present invention, the surgical instrument navigation system 10 may be further adapted to display four-dimensional image data for a region of interest as shown in FIG. 5. In this case, the imaging device 14 is operable to capture volumetric scan data 62 for an internal region of interest over a period of time, such that the region of interest includes motion that is caused by either the cardiac cycle or the respiratory cycle of the patient 13. A volumetric perspective view of the region may be rendered 64 from the volumetric scan data 62 by the data processor 16 as described above. The four-dimensional image data may be further supplemented with other patient data, such as temperature or blood pressure, using coloring coding techniques.

In order to synchronize the display of the volumetric perspective view in real-time with the cardiac or respiratory cycle of the patient, the data processor 16 is adapted to receive a timing signal from the timing signal generator 26. As described above, the timing signal generator 26 is operable to generate and transmit a timing signal that correlates to either the cardiac cycle or the respiratory cycle of the patient 13. In this way, the volumetric perspective image may be synchronized 66 with the cardiac or respiratory cycle of the patient 13. The synchronized image 66 is then displayed 68 on the display 18 of the system. The four-dimensional synchronized image may be either (or both of) the primary image rendered from the point of view of the surgical instrument or the secondary image depicting the indicia of the position of the surgical instrument 12 within the patient 13. It is readily understood that the synchronization process is also applicable to two-dimensional image data acquire over time.

To enhance visualization and refine accuracy of the displayed image data, the surgical navigation system can use prior knowledge such as the segmented vessel structure to compensate for error in the tracking subsystem or for inaccuracies caused by an anatomical shift occurring since acquisition of scan data. For instance, it is known that the surgical instrument 12 being localized is located within a given vessel and, therefore should be displayed within the vessel. Statistical methods can be used to determine the most likely location; within the vessel with respect to the reported location and then compensate so the display accurately represents the instrument 12 within the center of the vessel. The center of the vessel can be found by segmenting the vessels from the three-dimensional datasets and using commonly known imaging techniques to define the centerline of the vessel tree. Statistical methods may also be used to determine if the surgical instrument 12 has potentially punctured the vessel. This can be done by determining the reported location is too far from the centerline or the trajectory of the path traveled is greater than a certain angle (worse case 90 degrees) with respect to the vessel. Reporting this type of trajectory (error) is very important to the clinicians. The tracking along the center of the vessel may also be further refined by correcting for motion of the respiratory or cardiac cycle, as described above.

The surgical instrument navigation system of the present invention may also incorporate atlas maps. It is envisioned that three-dimensional or four-dimensional atlas maps may be registered with patient specific scan data or generic anatomical models. Atlas maps may contain kinematic information (e.g., heart models) that can be synchronized with four-dimensional image data, thereby supplementing the real-time information. In addition, the kinematic information may be combined with localization information from several instruments to provide a complete four-dimensional model of organ motion. The atlas maps may also be used to localize bones or soft tissue which can assist in determining placement and location of implants.

While the invention has been described in its presently preferred form, it will be understood that the invention is capable of modification without departing from the spirit of the invention as set forth in the appended claims.

What is claimed is:

1. A surgical instrument navigation system, comprising:
a surgical instrument;
a tracking subsystem operable to capture in real-time position data indicative of the position of the surgical instrument;
a data processor adapted to receive scan data representative of a region of interest of a given patient and the position data from the tracking subsystem, the data processor being operable to render an image of the region of interest from a point of view which relates to position of the surgical instrument, the image being derived from the scan data; and
a display in data communication with the data processor, the display being operable to display the image of the patient.

2. The surgical navigation system of claim 1 wherein a volumetric perspective image is rendered from a point of view of the surgical instrument.

3. The surgical navigation system of claim 1 wherein the surgical instrument is further defined as at least one of a catheter, a guide wire, a pointer probe, a stent, a seed, an implant, or an endoscope.

4. The surgical navigation system of claim 1 further comprising an imaging device operable to capture and provide the scan data to the data processor.

5. The surgical navigation system of claim 4 wherein the imaging device is operable to capture volumetric scan data or surface data representative of the region of interest.

6. The surgical navigation system of claim 4 wherein the imaging device is further defined as at least one of a magnetic resonance imaging device, a computed tomography imaging device, a positron emission tomography imaging device, a fluoroscopic imaging device, or an ultrasound imaging device.

7. The surgical navigation system of claim 1 wherein the tracking subsystem is further defined as an electro-magnetic localizing device having one or more electro-magnetic sensors attached to the surgical instrument.

8. The surgical navigation system of claim 7 wherein a volumetric perspective image is rendered from a point of view which correlates to one of the electro-magnetic sensors attached to the surgical instrument.

9. The surgical navigation system of claim 1 wherein the data processor is operable to render a second image of the region of interest based on the scan data, and to superimpose an indicia of the surgical instrument onto the second image of the patient.

10. The surgical navigation system of claim 9 wherein the data processor is further operable to track in real-time the position of the surgical instrument as it is moved within the region of interest and update the corresponding position of the indicia of the surgical instrument on the second image of the patient.

11. The surgical navigation system of claim 9 wherein the data processor is further operable to track in real-time the location and orientation of the surgical instrument as it is moved within the region of interest and the display is further operable to display the location and orientation of the surgical instrument.

12. A surgical instrument navigation system, comprising:
a surgical instrument;
a timing signal generator operable to generate and transmit a timing signal that correlates to at least one anatomical function of the patient;
a tracking subsystem operable to receive the timing signal from the timing signal generator, the tracking subsystem operable to capture position data indicative of the position of the surgical instrument and to report the position data in response to the timing signal received from the timing signal generator;
a data processor adapted to receive scan image data representative of an internal region of interest within a given patient and the position data from the tracking subsystem, the data processor being operable to render a volumetric perspective image of the internal region of interest from the scan image data and to superimpose an indicia of the surgical instrument onto the volumetric perspective image based on the position data received from the tracking subsystem; and
a display in data communication with the data processor, the display being operable to display the volumetric perspective image of the patient.

13. The surgical instrument navigation system of claim 12 wherein the timing signal correlates at least one of cardiac cycle or respiratory cycle of the patient.

14. The surgical instrument navigation system of claim 13 wherein the timing signal is generated at a repetitive point within each cycle of either the cardiac cycle or the respiratory cycle of the patient, thereby minimizing any jitter of the surgical instrument in the volumetric perspective image which may be caused by the cardiac cycle or the respiratory cycle of the patient.

15. The surgical instrument navigation system of claim 13 wherein the timing signal is at least one derived from or is an electrocardiogram signal from the patient.

16. The surgical instrument navigation system of claim 12 wherein the data processor is further operable to track position of the surgical instrument as it is moved within the region of interest and to update the corresponding position of the indicia of the surgical instrument in the volumetric perspective image of the patient.

17. The surgical navigation system of claim 12 wherein the data processor is further operable to track in real-time the location and orientation of the surgical instrument as it is moved within the region of interest and the display is further operable to display the location and orientation of the surgical instrument.

18. The surgical navigation system of claim 12 wherein the surgical instrument is further defined as at least one of a catheter, a guide wire, a pointer probe, a stent, a seed, an implant, or an endoscope.

19. The surgical navigation system of claim 12 further comprises an imaging device operable to capture and provide the scan image data to the data processor.

20. The surgical navigation system of claim 19 wherein the imaging device is operable to capture volumetric scan data representative of the internal region of interest.

21. The surgical navigation system of claim 19 wherein the imaging device is further defined as at least one of a magnetic resonance imaging device, a computed tomography imaging device, a positron emission tomography imaging device, a fluoroscopic imaging device, or a ultrasound imaging device.

22. The surgical navigation system of claim 12 wherein the tracking subsystem is further defined as an electromagnetic localizing device having one or more electromagnetic sensors attached to the surgical instrument.

23. A surgical instrument navigation system, comprising:
   a surgical instrument;
   an imaging device operable to capture volumetric scan data over time, the volumetric scan data representative of an internal region of interest within a patient and the internal region of interest having motion that is caused by at least one anatomical function of the patient;
   a timing signal generator operable to generate and transmit a timing signal that correlates to the at least one anatomical function of the patient;
   a data processor adapted to receive the volumetric image data from the imaging device and the timing signal from the timing signal generator, the data processor being operable to render a volumetric perspective image from the viewpoint of the surgical instrument of the internal region of interest over time, the volumetric perspective image being derived from the volumetric scan data and synchronized with the timing signal; and
   a display in data communication with the data processor, the display being operable to display the volumetric perspective image of the patient.

24. The surgical instrument navigation system of claim 23 wherein the timing signal correlates at least one of cardiac cycle or respiratory cycle of the patient.

25. The surgical instrument navigation system of claim 23, further comprising:
   a tracking subsystem operable to receive the timing signal from the timing signal generator, the tracking subsystem operable to capture position data indicative of a position of the surgical instrument and to report the position data in response to the timing signal received from the timing signal generator;
   a display in data communication with the data processor, the display being operable to display the volumetric perspective image of the patient based upon the position of the surgical instrument.

26. A surgical instrument navigation system, comprising:
   a non-imaging surgical instrument;
   a tracking subsystem operable to capture in real-time position data indicative of the position of the non-imaging surgical instrument;
   a data processor adapted to receive scan data representative of a region of interest of a given patient and the position data from the tracking subsystem, the data processor being operable to render an image of the region of interest from a point of view which relates to the position of the surgical instrument; and
   a display in data communication with the data processor, the display being operable to display the image of the patient;
   wherein the rendered image being derived from the scan data.

* * * * *